(12) United States Patent
Buchanan

(10) Patent No.: US 8,025,676 B2
(45) Date of Patent: Sep. 27, 2011

(54) BIOABSORBABLE IMPLANTABLE STRUCTURE

(75) Inventor: Fraser James Buchanan, Co. Antrim (IE)

(73) Assignee: The Queen's University of Belfast, Belfast (GB)

( * ) Notice: Subject to any disclaimer, the term of this patent is extended or adjusted under 35 U.S.C. 154(b) by 1061 days.

(21) Appl. No.: 10/589,037

(22) PCT Filed: Feb. 10, 2005

(86) PCT No.: PCT/GB2005/000471
§ 371 (c)(1),
(2), (4) Date: Nov. 14, 2006

(87) PCT Pub. No.: WO2005/077431
PCT Pub. Date: Aug. 25, 2005

(65) Prior Publication Data
US 2008/0021569 A1  Jan. 24, 2008

(30) Foreign Application Priority Data
Feb. 10, 2004  (GB) .................................. 0402838.7

(51) Int. Cl.
*A61B 17/04* (2006.01)
*A61L 17/00* (2006.01)
*A61F 2/02* (2006.01)
*H01J 37/30* (2006.01)

(52) U.S. Cl. ..... 606/230; 606/228; 606/231; 623/23.75; 264/485

(58) Field of Classification Search ............ 623/23, 623/23.75; 523/111, 113; 606/228, 230, 606/231; 264/485
See application file for complete search history.

(56) References Cited

U.S. PATENT DOCUMENTS

| 5,530,037 | A | * | 6/1996 | McDonnell et al. | ............ 522/79 |
| 5,788,979 | A | * | 8/1998 | Alt et al. | ........................ 424/426 |
| 5,889,075 | A | * | 3/1999 | Roby et al. | ........................ 522/87 |
| 6,494,917 | B1 | | 12/2002 | McKellop et al. | .......... 623/23.58 |
| 6,716,444 | B1 | * | 4/2004 | Castro et al. | ................... 424/422 |
| 7,144,976 | B2 | * | 12/2006 | Matsuda et al. | ............... 528/354 |
| 2004/0133237 | A1 | * | 7/2004 | Shalaby | ........................ 606/230 |
| 2005/0276841 | A1 | * | 12/2005 | Davis et al. | .................... 424/443 |
| 2007/0078513 | A1 | * | 4/2007 | Campbell | .................... 623/1.44 |

FOREIGN PATENT DOCUMENTS

| GB | 2 141 435 | 12/1984 |
| WO | WO 02/48259 | 6/2002 |
| WO | WO 2004/026361 | 4/2004 |

OTHER PUBLICATIONS

Coqueret, "Electron Beam Processing and Polymeric Materials: Technological Aspects and Chemical Modifications", *Journal of Polymer Engineering*, vol. 15, No. 1/2, 1995, pp. 117-131.
Yip, et al., "Sustained release system for highly water-soluble radiosensitizer drug etanidazole: irradiation and degradation studies", *Biomaterials*, vol. 24, No. 11, May 2003, pp. 1977-1987.

(Continued)

*Primary Examiner* — Mark Eashoo
*Assistant Examiner* — Angela C Scott
(74) *Attorney, Agent, or Firm* — Drinker Biddle & Reath LLP

(57) ABSTRACT

Provided is a method of producing a bioabsorbable, implantable substrate having a graded molecular weight distribution, comprising exposing at least a portion of the implantable substrate to electron beam irradiation. There is also provided a bioabsorbable, implantable substrate comprising a bioabsorbable polymer having a graded molecular weight distribution through at least a portion of its thickness.

11 Claims, 3 Drawing Sheets

Bioabsorption behaviour of implantable substrates according to the present invention Implantation time

OTHER PUBLICATIONS

Collett, et al., "Gamma-Irradiation of Biodegradable Polyesters in Controlled Physical Environments", Papers Presented at the Meeting—American Chemical Society, Division of Polymer Chemistry, vol. 30, No. 1, Apr. 14, 1989, pp. 468-469.

Maggi, et al., "Chemical and Physical Stability of Hydroxypropylmethylcellulose Matrices Containing Diltiazem Hydrochloride after Gamma Irradiation", *Journal of Pharmaceutical Sciences*, vol. 92, No. 1, Jan. 2003, pp. 131-141 (abstract).

* cited by examiner

BIOABSORBABLE IMPLANTABLE STRUCTURE

REFERENCE TO RELATED APPLICATIONS

This application is filed as a US National Phase filing of PCT application PCT/GB2005/000471, having an International filing date of 10 Feb. 2005; published as WO 2005/077431, 25 Aug. 2005; and claiming priority to GB Application 0402838.7, filed 10 Feb. 2004, each of which is herein incorporated in its entirety.

FIELD OF THE INVENTION

The present invention relates to a method of producing a bioabsorbable implantable substrate, a method of altering the rate of bioabsorbability of a least a portion of a bioabsorbable implantable substrate, and a bioabsorbable implantable substrate, having graded molecular weight distribution formed according to these methods.

BACKGROUND

The long-term goal of biomaterials research lies in tissue regeneration, not replacement. In 'tissue engineering' biocompatible structures can be used either to engineer in-vitro living cellular constructs for transplantation, or to temporarily support load and facilitate in-vivo mechanisms for tissue regeneration. The ideal material for these purposes should provide high strength initially, then gradually degrade, transferring mechanical loads to regenerating tissue. Typical surgical applications are in the repair of connective soft tissue, ligaments or tendons and hard tissue such as bone.

In applications where tissue only requires temporary support or fixation the use of bioabsorbable polymers is appropriate. Depending on the choice of material and processing conditions, bioabsorbable polymers may retain their tissue supporting properties for days, weeks or months. Advantages of these materials are firstly, reduced risk of long-term complications because stresses are eventually transferred to the healing tissue, and secondly, the avoidance of the necessity for a retrieval operation.

Current trends in orthopaedic practice and research suggest that the most important bioabsorbable polymers used in surgery are synthetic polymers such as aliphatic polyesters (e.g. polyglycolide (PGA), polylactide (PLA) and their copolymers). These polyesters degrade in-vivo by hydrolysis into lactic acid and glycolic acid, which are then incorporated in the tricarboxylic acid cycle and excreted. These types of polymer generally degrade by bulk erosion, as the rate at which water penetrates the material exceeds the rate at which chain scission (into water-soluble fragments) occurs within the polymer [Middleton, J. C., Tipton, A. J., *Biomaterials*, 2335-2346, 2000]. Degradation in the interior of the device may occur faster than on the surface due to autocatalysis. The implication of this is that the device remains as a space-filler long after the useful strength of the polymer has deteriorated. The ingrowth of natural tissue is prevented, and a 'lactide-burst' of low pH material may be released when the surface of the implant is finally degraded which can damage surrounding cells and cause inflammation.

SUMMARY OF THE INVENTION

The invention advantageously provides a method of producing a bioabsorbable, implantable substrate having a graded molecular weight distribution, wherein the method comprises providing an implantable substrate and altering the molecular weight distribution of at least a portion of, or the entire surface of, the implantable substrate by exposing that portion of the implantable substrate to electron beam irradiation. The irradiation may be provided as one or more beams, each of which may be at a different intensity, and each of which may penetrate to a different depth.

It is a further object of the invention to provide a bioabsorbable, implantable substrate produced by the disclosed method, wherein the molecular weight distribution of at least a portion of, or the entire surface of, the implantable substrate has been altered by exposing that portion of the implantable substrate to the electron beam irradiation. In one embodiment, the bioabsorbable implantable substrate comprises a bioabsorbable polymer having a graded molecular weight distribution through at least a portion of, or the whole of, its thickness.

It is also an object of the invention to provide a method of modifying a rate of bioabsorbability of at least a portion of a bioabsorbable, implantable substrate, wherein the method comprises exposing that portion of the implantable substrate to electron beam irradiation.

In an additional object of the invention, there is provided a method of treating a disorder of, or damage to, hard or soft tissue in a human or animal subject in need of such treatment, wherein the method comprises of implanting a bioabsorbable, implantable substrate of the invention into the human or animal body to treat, repair or replace the diseased or damaged hard or soft tissue. Also provided is a method of using the implanting a bioabsorbable, implantable substrate of the invention in manufacturing a medicament or medical device for the repair, treatment or replacement of diseased or damaged hard or soft tissue of in a human or animal subject.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended drawings. It should be understood, however, that the invention is not limited to the precise arrangements and instrumentalities shown.

DETAILED DESCRIPTION OF CERTAIN EMBODIMENTS OF THE INVENTION

Figure 1:
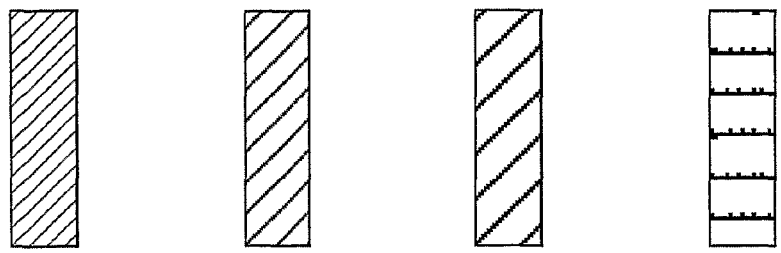
FIG. 1 is an illustration showing the bioabsorption behaviour of an implantable substrate known in the art wherein diagonal hatching represents the degradation rate and molecular weight of the substrate and increased width of hatching indicates increased degradation rate and decreased molecular weight and wherein horizontal hatching represents fragmentation of the substrate.

According to a first aspect of the present invention there is provided a method of producing a bioabsorbable, implantable substrate having a graded molecular weight distribution, comprising the steps of providing an implantable substrate and altering the molecular weight distribution of at least a portion of the implantable substrate by exposing that portion of the implantable substrate to electron beam irradiation.

Advantageously the molecular weight distribution of the portion of the implantable substrate exposed to electron beam irradiation is reduced.

Preferably at least a portion of the surface of the implantable substrate is exposed to electron beam irradiation. Suitably the molecular weight distribution of the entire surface or body of the implantable substrate is altered by exposing the entire surface of the implantable substrate to electron beam irradiation.

At least a portion of the implantable substrate may be exposed to electron beam irradiation for 0.1 to 100 seconds; suitably for 1 to 90 seconds; more suitably 3 to 60 seconds.

The electron beam irradiation may have an intensity of 0.1 to 20 MeV; suitably 0.5 to 15 MeV; more suitably 1 to 5 MeV. A total radiation dose of 1 to 100 kGy may be applied to the implantable substrate. In one embodiment the implantable substrate may be subject to more than one dose of radiation; suitably 2 to 4 doses of radiation. Each dose of radiation may be 1 to 50 kGy.

Suitably the electron beam irradiation penetrates 0.1 to 50 mm from the surface of the implantable substrate; more suitably the electron beam irradiation penetrates 2 to 20 mm. In one embodiment the electron beam irradiation penetrates 2 to 15 mm.

The implantable substrate may have a wall thickness of at least 50 mm; suitably of 15 mm or less; more suitably of 5 mm or less.

In one embodiment the flexural strength of the portion of the implantable substrate exposed to electron beam irradiation is altered; suitably reduced.

In one embodiment the percentage mass loss of the portion of the implantable substrate exposed to electron beam irradiation is altered; suitably reduced.

Preferably the exposure to electron beam irradiation also causes sterilisation of the implantable substrate.

The method may comprise the step of exposing the implantable substrate to one or more doses of electron beam irradiation. Each dose of electron beam irradiation may be at a different intensity.

Suitably each dose of electron beam irradiation penetrates the implantable substrate to a different depth. The molecular weight distribution, and thus the rate of biodegradation of the implant is suitably different at different depths.

According to a second aspect, the present invention also provides a method of modifying the rate of bioabsorbability of at least a portion of a bioabsorbable, implantable substrate comprising the step of exposing that portion to electron beam irradiation.

According to a third aspect of the present invention there is provided a bioabsorbable, implantable substrate obtainable by either of the methods described above.

According to a fourth aspect of the present invention, there is provided a bioabsorbable implantable substrate comprising a bioabsorbable polymer having a graded molecular weight distribution through at least a portion of its thickness.

According to a fifth aspect of the present invention, there is provided a bioabsorbable implantable substrate having an outer surface and a core wherein the molecular weight distribution of the implantable substrate is greater at the core than towards the outer surface, and the core is less bioabsorbable than towards the outer surface.

Preferably the bioabsorbable implantable substrate of the present invention is bioabsorbable at a predetermined rate.

The implantable substrate of the present invention may have a graded molecular weight distribution through at least a portion of its thickness from its surface thickness to the complete thickness of the implantable substrate. The molecular weight distribution of the implantable substrate may be lower towards the surface, causing the rate of bioabsorbability to be higher towards the surface. The rate of bioabsorbability may be pre-determined and controlled by altering the molecular weight distribution of the implantable substrate. The initial strength and average strength during degradation of the implantable substrate of the present invention are therefore also predictable and controllable.

In one embodiment, the outer surface of the implantable substrate biodegrades initially and the load bearing strength of the substrate is retained from the core. The implantable substrate of the present invention thus allows the ingrowth of natural tissue, whilst still providing some structural support.

Preferably the outer surface and the core of the bioabsorbable implantable substrate are formed from the same material.

In general the bioabsorbable implantable substrate is suitably formed from aliphatic polyesters such as polyglycolide (PGA), polycaprolactone, polylactide (PLA), poly(dioxanone) (PDO), poly(glycolide-co-trimethylene carbonate) (PGA-TMC), polyanhydrides, poly(propylene fumarate), polyurethane and copolymers.

The molecular weight distribution of the substrate is dependent on the material of the implantable substrate, but suitably the molecular weight distribution of the outer surface of the implantable substrate is from 10,000 to 200,000 and the molecular weight distribution of the core of the implantable substrate is from 100,000 to 500,000. Preferably the molecular weight distribution of the implantable substrate changes gradually from the surface to the core.

The rate of absorption of the implantable substrate into the body is dependant upon the material of the implantable substrate and the size of the implantable substrate. However, the rate of absorption of the implantable substrate of the present invention may preferably be pre-determined and controlled to suit its purpose.

Preferably the implantable substrate is bioabsorbed within 20 to 365 days, more preferably 60 to 120 days.

The bioabsorbable implantable substrate of the present invention may comprise additives such as bioactive agents and drugs. The additives may be incorporated into the bioabsorbable polymer to enhance tissue regeneration or reduce implant-related infection. The rate of release of the additives is not necessarily linear, and is dependent upon the absorption rate of the polymers, but is typically released over 20 to 175 days. The bio-active agents are released in a controlled manner as the outer surface of the implantable substrate biodegrades, and later as the core biodegrades. As such, the bio-active agents may be released as and when required to enhance tissue remodelling, and/or minimise the risk of infection.

Preferably the implantable substrate is an interference screw, suture anchor, bioresorbable polymer composite (which is suitably self-reinforced), or a bioabsorbable scaffold for tissue regeneration and growth.

The implantable substrate may cultivate tissue in-vivo or in-vitro.

According to a sixth aspect of the present invention there is provided the use of the bioabsorbable implantable substrate hereinbefore described, in the repair or treatment of disorders of or damage to hard or soft tissue.

According to a seventh aspect of the present invention there is provided a method of treatment of a disorder of, or damage to hard or soft tissue comprising the step of implanting the bioabsorbable implantable substrate as hereinbefore defined in a human or animal body.

According to an eighth aspect of the present invention there is provided the bioabsorbable implantable substrate as hereinbefore defined for use in therapy.

Suitably the hard or soft tissue may be connective tissue, ligaments, tendons or bone.

The disorder may be any tissue defect or trauma including osteo or rheumatoid arthritis, osteoporosis, inflammatory, neoplastic, traumatic and infectious tissue conditions, syndromes characterised by chondrodysplasia, cartilage damage, fracture, ligament tears, hernia, synovitis, systemic lupus erthematosus, or wounds, particularly those sustained during surgery.

The degradation rate of bioabsorbable polymers is at least partially dependent on their initial molecular weight. The higher the initial molecular weight the longer the bioabsorption time (if all other factors are kept similar). It is now well established that bioabsorbable polymers degrade by essentially the same mechanism—hydrolytic scission of the ester bonds. The reaction is autocatalytic and follows pseudo first order reaction kinetics:

$$M_n = M_{n,o} e^{-kt},$$

wherein:
Mn=molecular weight at a time from implantation;
$M_{n,o}$=initial molecular weight;
e=exponential function;
k=constant;
t=time from implantation.

K is suitably 1 to $9 \times 10^{-6}$ s$^{-1}$. K is typically $1.16 \times 10^{-6}$ s$^{-1}$ for polyglycolides.

Therefore if the initial molecular weight of a polymer is known, the degradation rate can be predicted. The decrease in strength with time is also predictable from the molecular weight, using the equation:

$$\sigma = \sigma_\infty - \frac{B}{M_n}$$

wherein:
σ=strength at a time (t) from implantation;
$\sigma_\infty$=initial strength;
B=constant.

B is suitably 1 to $9 \times 10^5$ MPa g$^{-1}$ mol. B is typically $3 \times 10^5$ MPa g$^{-1}$ mol for polyglycolides.

The penetration depth for electron beam irradiation depends on the energy of the electrons used and the density of the absorbing material. Penetration depth can be predicted from the expression:

$$d = \frac{(0.524E - 0.1337)}{\rho}$$

$d$ = depth (cm);
$E$ = electron energy (MeV);
$\rho$ = density (gcm$^{-3}$).

The typical densities of polyesters such as PGA and PLLA are in the range 1.0-1.5 gcm$^{-3}$, therefore electron penetration depth for energies in the range 0.3 to 10 MeV would be approximately 0.2 mm to 40 mm. The energy of a 10 MeV electron beam accelerator can be reduced by the use of metallic shielding of various thicknesses.

The present invention will now be described by way of example, with reference to the accompanying drawings.

FIG. 1 shows that upon implantation in a human or animal body known implantable substrates undergo a loss in strength and mass across their entire cross-section. Known implantable substrates have an even molecular weight distribution across their thickness and so the core and surface of known implantable substrates are bioabsorbed at approximately the same rate. The space occupied by known implantable substrates does not reduce until the known implant is almost entirely bioabsorbed.

After implantation for a prolonged period of time, known implantable substrates undergo fragmentation due to a loss in mass. The core of such an implantable substrate fragments before the surface which may result in a "lactide-burst" of low pH material which can damage surrounding cells and cause inflammation.

Figure 2:
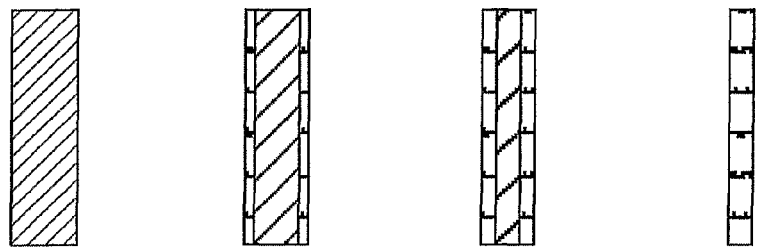
FIG. 2 is an illustration showing the bioabsorption behaviour of an implantable substrate according to the present invention wherein diagonal hatching represents the degradation rate and molecular weight of the substrate and increased width of hatching indicates increased degradation rate and decreased molecular weight and wherein horizontal hatching represents fragmentation of the substrate.

FIG. 2 shows an implantable substrate according to the present invention, and shows how the implantable substrate is bioabsorbed upon implantation into a human or animal body. The implantable substrate of the present invention has a graded molecular weight distribution, wherein the surface of the implantable substrate has a lower molecular weight distribution than the core.

The surface of the implantable substrate is bioabsorbed at a faster rate than the core of the implantable substrate, such that the surface of the implantable substrate undergoes loss in strength before the core and the space occupied by the implantable substrate is reduced gradually, thus allowing greater tissue ingrowth into the space occupied by the implant.

The core of the implantable substrate may still fragment but is bioabsorbed after the surface of the implantable substrate. The space occupied by the implantable substrate is reduced gradually during bioabsorption, encouraging tissue ingrowth.

The invention is further defined by reference to the following specific, but nonlimiting, examples. It will be apparent to those skilled in the art that many modifications, both to materials and methods, may be practiced without departing from the purpose or narrowing the scope of this invention.

EXAMPLES

Example 1

Poly (L-lactide) PLLA was moulded into sheets with a thickness of approximately 0.9 mm in a Collin P 200 P platen press at temperatures increasing to 200° C. and pressures increasing to 100 bar. The PLLA used was from Resomer® L (Batch Number 26033), supplied in pellet form by Boehringer Ingelheim (Ingelheim, Germany). Gel Permeation Chromatography of the material gave the molecular weight as 462,000 (expressed as polystyrene molecular weight equivalent) and the Mn number (average molecular weight) as 166,000 (expressed as polystyrene molecular weight equivalent). The sheets were then manufactured into ISO 527-2 standard tensile samples approximately 75 mm in length using a hand operated table press. The samples were then annealed in an oven at 120° C. for 4 hours to give a more realistic representation of processed material.

In order to study the effects of e-beam radiation on the PLLA materials at different depths within a bulk of material, spacers with similar material properties to PLLA were required. Sheets of acrylic having a similar density to the PLLA samples were chosen. The samples and the acrylic sheet spacers were stacked and 28 tensile PLLA samples were irradiated at 5 different depths; namely 0 mm, 3.9 mm, 13.9 mm, 27.3 mm and 42.7 mm from the surface of the composite structures. The stacked samples and spacers were framed by acrylic sheets with a wall thickness of at least 50 mm. This ensured that radiation reached the PLLA samples from the intended direction only. The samples were then irradiated at Ebis Iotron (Didcot, Oxfordshire) using a 10 MeV electron beam machine. The radiation dose was set to give the upper surface of the composite sample, and therefore the 0 mm depth PLLA samples, a radiation dose of 40 kGy. The samples were stored in a desiccator cupboard following irradiation.

The medium used for the in vitro degradation of the PLLA samples was a "Sörensen" pH 7.4 buffer solution prepared from potassium dihydrogenphosphate ($KH_2PO_4$) and disodium hydrogenphosphate ($Na_2HPO_4$). These salts were mixed into a solution in a ratio of 1:15 mol/l. The solutions were then combined at a ratio of 18.2% $KH_2PO_4$ solution and 81.8% $Na_2HPO_4$ solution. This ratio is set out by ISO 15814: "Implants for surgery—Copolymers and blends based on polylactide—In Vitro degradation testing". Each tensile sample of PLLA material was weighed before being placed in a vial with approximately 20 ml of buffer solution. The vials were then placed in an oven at 70° C. At specified time periods, 5 samples from each depth were removed, and then blot dried and weighed for water uptake measurements. The samples were then tensile tested using an Instron Universal materials testing machine in accordance with ISO 527-2. After testing, the samples were dried and weighed to obtain mass loss results. Gel Permeation Chromatography was carried out on the tested samples to determine the molecular weight of the degraded PLLA. The results were compared to a control sample which had not been exposed to e-beam irradiation.

The irradiated samples were subject to temperatures of up to 70° C. for one day to induce accelerated degradation and the flexural strength of the samples were recorded immediately after e-beam irradiation and after accelerated degradation had been induced. The results were compared to a control sample which had not been exposed to e-beam irradiation.

A mass-loss study was designed to determine how the irradiation had affected the resorption rate of the polymer. To assess this accelerated degradation was induced. To allow four time points, with three repetitions at each, 12 samples were prepared for each cross-sectional depth and for the control. Each sample weighed approximately 0.085 g. The samples were dried in a vacuum oven at 37° C. for 48 hours before being individually weighed, and their masses recorded. The samples were then placed in "Sörensen" pH 7.4 buffer-solution, as described previously, and stored in an oven at 70° C. After set periods of times three samples from each set were removed from the oven. The samples and buffer solution were filtered using hardened ashless filter paper. The filtrate was then rinsed with deionised water and re-filtered. The filter paper containing the filtrate was then dried in an oven at 80° C. for at least 3 hours—before being cooled to room temperature. The dried filtrate was then removed and weighed. Through comparison of the mass of the dried filtrate with the original mass of the sample, the percentage mass loss was determined. A control sample which had not been exposed to e-beam irradiation was also analysed.

Figure 3:
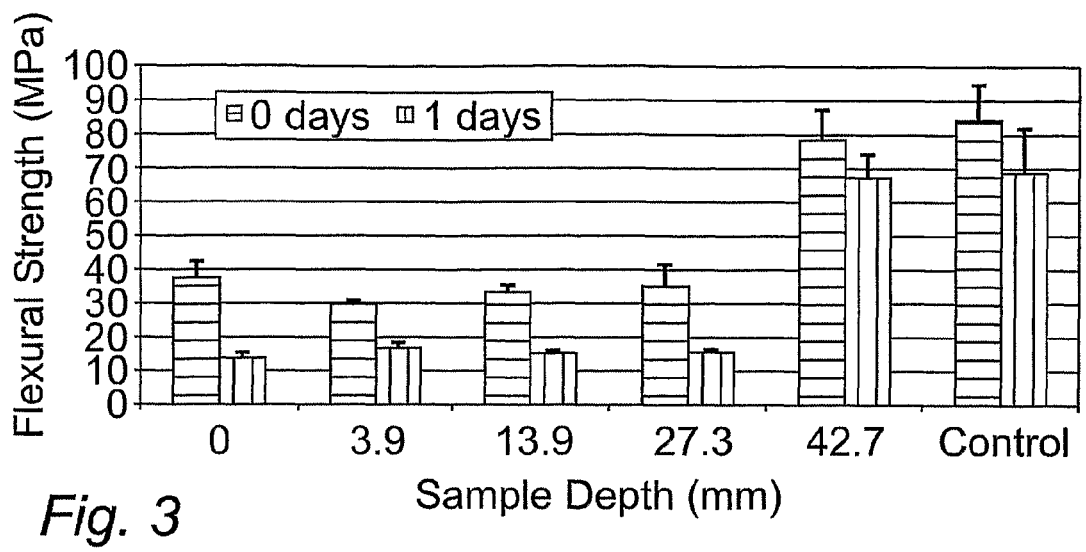
FIG. 3 shows the flexural strength of implantable substrates formed according to the method of Example 1 at different depths from the surface of the implantable substrate immediately after exposure to e-beam irradiation (0 days) and after exposure for 1 day to conditions which induce accelerated degradation (1 day)

The results of the flexural strength tests are summarised in FIG. 3. Upon exposure to e-beam irradiation the flexural strength towards the surface of the sample (0 to 27.3 mm) was reduced. The flexural strength at the core (i.e. 42.7 mm from the surface) was approximately the same as the flexural strength of the control sample and this may suggest that the e-beam irradiation did not penetrate to the core of the sample. The flexural strength of all samples decreased after accelerated degradation had been induced. The flexural strength of samples at the core (42.7 mm from the surface) remained approximately the same as the flexural strength of the control sample after accelerated degradation. The flexural strength results suggest that implantable substrates exposed to e-beam irradiation would have a tendency to biodegrade gradually from the surface inwards.

Figure 4:
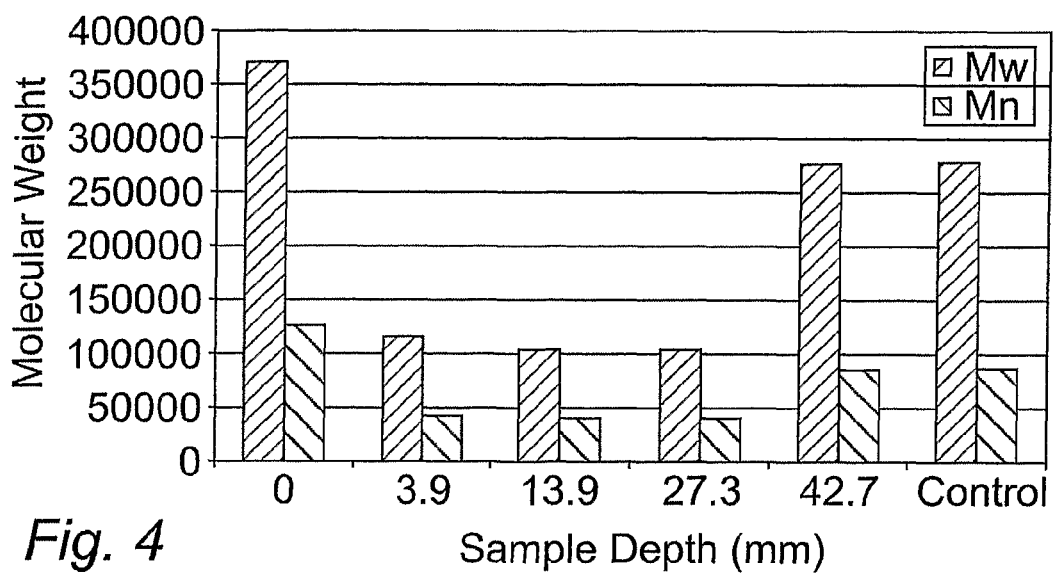
FIG. 4 shows the polystyrene molecular weight equivalent (Mw) and the average molecular weight (Mn) of implantable substrates formed according to the method of Example 1 at different depths from the surface of the implantable substrate.

The results of the molecular weight tests are summarised in FIG. 4. A control sample which had not been exposed to any e-beam irradiation was also analysed. Two measures of molecular weight were taken from the samples: polystyrene molecular weight equivalent (Mw) and average molecular weight (Mn). Upon exposure to e-beam irradiation the molecular weight (both Mw and Mn) of the implantable substrate was reduced at depths of 3.9 to 27.3 mm from the surface. The molecular weight at the core (i.e. 42.7 mm from the surface) remained approximately the same as the molecular weight of the control and this may suggest that the e-beam irradiation did not penetrate to the core of the sample. The molecular weight at the surface (0 mm) was unexpectedly high after exposure to e-beam irradiation. This suggests that the implantable substrate may have been exposed to too high a dose of e-beam irradiation and that this may have induced some cross-linking of the polymer at the surface thus increasing the molecular weight at the surface. The molecular weight results suggest that implantable substrates exposed to e-beam irradiation have a graded molecular weight distribution from the surface to the core, the molecular weight being greatest at the core. Implantable substrates exposed to e-beam irradiation would have a tendency to biodegrade gradually from the surface inwards, reducing the space occupied by the implantable substrate gradually. However, if too high a dose of e-beam irradiation is used cross-linking of the substrate polymer may be induced at the surface leading to a relatively high molecular weight at the surface. This effect may be avoided by reducing the dose of e-beam irradiation used.

Figure 5:
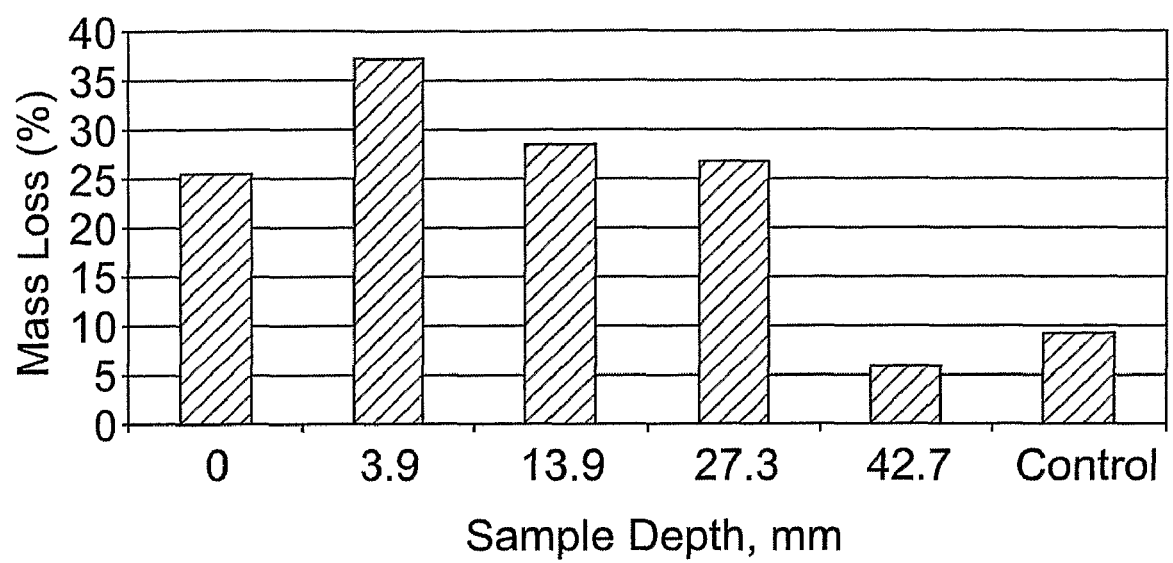
FIG. 5 shows the percentage mass loss of implantable substrates formed according to the method of Example 1 at different depths from the surface of the implantable substrate after exposure for 12 days to conditions which induce accelerated degradation.

FIG. 5 summarises the results of the mass loss tests. Upon exposure to e-beam irradiation the percentage mass loss towards the surface (0 to 27.3 mm) was increased compared to the control. The percentage mass loss of the surface was lower than the percentage mass loss at slightly greater depths. This may suggest that the dose of e-beam irradiation was too high and induced some degree of cross-linking on the surface. This was also suggested by the molecular weight analysis. The percentage mass loss of the core (42.7 mm) is approximately the same as the percentage mass loss of the control and this may suggest that the e-beam irradiation did not penetrate the core of the sample. The mass loss results indicate that implantable substrates exposed to e-beam irradiation would have a tendency to biodegrade gradually from the surface inwards.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

The invention claimed is:

1. A bioabsorbable, implantable substrate comprising an outer surface and a core, said implantable substrate having a molecular weight distribution that changes gradually from the outer surface to the core wherein the average molecular weight at the core is greater than the average molecular weight at the entire outer surface, the entire surface of the implantable substrate having been exposed to electron beam irradiation to reduce the molecular weight distribution of said entire surface, wherein the rate of bioabsorbability of the core is less than the rate of bioabsorbability of the entire outer surface.

2. The substrate of claim 1, wherein the rate of bioabsorbability of the implant is predetermined.

3. The substrate of claim 1, wherein the outer surface and the core of the bioabsorbable implantable substrate are formed from the same material.

4. The substrate of claim 1, comprising a composition selected from polyglycolide (PGA), polycaprolactone, polylactide (PLA), poly(dioxanone) (PDO), poly(glycolide-co-trimethylene carbonate) (PGA-TMC), polyanhydrides, poly(propylene fumarate), polyurethane, and copolymers thereof and combinations thereof.

5. The substrate of claim 1, formed into an interference screw, a suture anchor, a bioresorbable polymer composite, or a bioabsorbable scaffold for tissue regeneration and growth.

6. A method of treating a disorder of, or damage to, hard or soft tissue in a human or animal subject in need of such treatment, said method comprising the step of implanting the substrate of claim 1 into the human or animal body to treat, repair or replace the diseased or damaged hard or soft tissue.

7. The method of claim 6, wherein the disorder is osteoarthritis; rheumatoid arthritis; osteoporosis; an inflammatory, neoplastic, traumatic or infectious tissue condition; a syndrome characterised by chondrodysplasia, synovitis, or systemic lupus erthematosus; or wherein the damage results from wounds sustained during surgery, cartilage damage, fracture, ligament tears, or hernia.

8. A method of producing a bioabsorbable, implantable substrate comprising an outer surface and a core, wherein the molecular weight distribution of the implant changes gradually from the outer surface to the core, the average molecular weight at the core is greater than the average molecular weight at the entire outer surface, and the rate of bioabsorbability of the core is less than the rate of bioabsorbability of the entire outer surface, said method comprising the steps of providing an implantable substrate and exposing the entire surface of the implantable substrate to electron beam irradiation to reduce the molecular weight distribution of said entire surface.

9. The method of claim 8, wherein the implantable substrate is exposed to one or more doses of electron beam irradiation having an intensity of 0.1 to 10 MeV for 0.1 to 100 seconds and the electron beam irradiation penetrates 0.1 to 40 mm from the surface of the implantable substrate.

10. The method of claim 8, wherein the implantable substrate is exposed to more than one dose of electron beam irradiation and each dose of electron beam irradiation is of a different intensity.

11. The method of claim 10, wherein each dose of electron beam irradiation penetrates the implantable substrate to a different depth.

* * * * *